United States Patent [19]

Hollis et al.

[11] Patent Number: 4,960,590

[45] Date of Patent: Oct. 2, 1990

[54] NOVEL POLYMERIC QUATERNARY AMMONIUM TRIHALIDES

[75] Inventors: C. George Hollis; S. Rao Rayudu, both of Germantown, Tenn.

[73] Assignee: Buckman Laboratories International, Inc., Memphis, Tenn.

[21] Appl. No.: 308,677

[22] Filed: Feb. 10, 1989

[51] Int. Cl.$^5$ .............. H61K 31/74; A01N 25/00; A01N 33/12; C08G 73/00

[52] U.S. Cl. .................... 424/78; 424/405; 514/642; 528/392; 528/397; 528/59; 528/422; 525/540

[58] Field of Search .............. 71/67; 424/405, 78; 523/122; 514/642; 528/392, 397, 59, 422; 525/540

[56] References Cited

U.S. PATENT DOCUMENTS

| | | |
|---|---|---|
| 2,881,070 | 4/1959 | Pera . |
| 3,771,989 | 11/1973 | Pera et al. ............... 514/642 |
| 3,778,476 | 12/1973 | Rembaum et al. ............ 525/539 |
| 3,874,870 | 4/1975 | Green et al. . |
| 3,898,336 | 8/1975 | Rembaum et al. ............ 424/447 |
| 3,931,319 | 1/1976 | Green et al. . |
| 4,018,592 | 4/1977 | Buckman ............... 71/67 |
| 4,025,627 | 5/1977 | Green et al. . |
| 4,027,020 | 5/1977 | Green et al. . |
| 4,054,542 | 10/1977 | Buckman et al. ........... 528/405 |
| 4,581,058 | 4/1986 | Fenyes et al. ............ 514/63 |
| 4,789,489 | 12/1988 | Hollis et al. ............. 71/67 |

OTHER PUBLICATIONS

Moody, CA 107(16): 140834c, 1986, Synergistic Microbiocide Composition for Water Treatment.

Primary Examiner—Merrell C. Cashion, Jr.
Assistant Examiner—Carmen B. Pili-Curtis
Attorney, Agent, or Firm—Finnegan, Henderson, Farabow, Garrett & Dunner

[57] ABSTRACT

Polymeric quaternary ammonium trihalides, preferably triiodides, and use of polymeric quanternary ammonium trihalides to inhibit the growth of microorganisms in aquatic systems, to disinfect or sanitize surfaces and to disinfect the skin of animals, including humans.

9 Claims, No Drawings

NOVEL POLYMERIC QUATERNARY AMMONIUM TRIHALIDES

This invention encompasses polymeric quaternary ammonium trihalides, particularly triiodides, and their use as general microbicides, particularly as bactericides and fungicides, for aqueous systems, as surface, particularly hard surface, disinfectants or sanitizers, and as disinfectants for animal skin, including the skin of humans.

BACKGROUND OF THE INVENTION

Polymeric quaternary ammonium compounds (also known as ionene polymers or polymeric quats) containing chlorides and bromides as anions have been shown to be aquatic bactericides and algicides (U.S. Pat. Nos. 3,874,870, 3,931,319, 4,027,202, and 4,581,058). In fact, Busan® 77 polymer, an ionene chloride, is sold commerically as an algicide and bactericide for various aquatic systems, such as water cooling devices, swimming pools, and fresh water holding tanks However, these polymeric quats could stand improvement. In particular, it would be significant to develop polymeric quats that are even better fungicides, and also are faster in killing bacteria.

The present invention can constitute such an improvement and describes compounds, some of which are novel, which contain trihalide as the counter ion to the quaternary nitrogens in the polymer chain and which are useful as aquatic microbicides, disinfectants for human skin, and surface disinfectants or sanitizers. Representative trihalides useful in the present invention include $Br_3^-$, $I_3^-$, $BrI_2^-$, $ClI_2^-$, $ClBr_2^-$ and $Br_2I^-$. $I_3^-$ is the preferred trihalide.

U.S. Pat. Nos. 3,778,476 and 3,898,336 describe the preparation of some of these compounds. The disclosure of these patents is specifically incorporated by reference herein. The compounds of these two patents are proposed therein for use in coating substrates to provide an antibacterial layer for an application such as surgical sutures. The present invention is the method of using ionene trihalides to disinfect or sanitize surfaces and provide microorganism control in aquatic systems and also includes some novel trihalide compounds.

SUMMARY OF THE INVENTION

The inventors have discovered a new method of inhibiting the growth of a microorganism in aquatic systems susceptible to the growth of such microorganism, a new method of disinfecting or sanitizing surfaces and a new method of disinfecting skin. The method uses ionene trihalides, preferably ionene triiodides, which can prevent the proliferation of microorganisms, such as bacteria, fungi, and algae, in various systems which contain or move water.

In particular, ionene trihalides can kill bacteria and fungi very quickly and can be functional as hard surface disinfectants used in hospitals, food handling facilities, and the like. The ionene trihalides can specifically be used to sanitize toilets and to disinfect the skin of humans and other animals.

The present invention also provides a composition of matter which is a polymeric quaternary ammonium compound having the formula

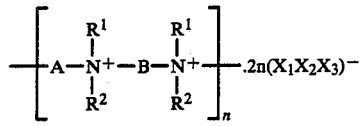

wherein $X_1$, $X_2$ and $X_3$ are each a halogen and can all be the same halogen or different halogens and wherein $R_1$ and $R^2$, which can all be the same or different, are selected from the group consisting of alkyl groups having from 1 to 20 carbon atoms and having either 0 or 1 hydroxyl substituent, a benzyl group, and a benzyl group bearing on the benzene moiety one alkyl group having from 2 to 20 carbon atoms; A is selected from the group consisting of a divalent hydrocarbon radical containing 1 to 10 carbon atoms, preferably an alkylene radical, and a divalent hydrocarbon radical containing 1 to 10 carbon atoms and also containing an oxygen atom as an ether group; B is a divalent hydrocarbon radical containing 1 to 10 carbon atoms, preferably an alkylene, aryl, arylalkylene or alkylenearylakylene radical, the hydrocarbon radical being substituted by at least one substituent selected from the group consisting of a hydroxyl group and a substituent substituted by at least one hydroxyl group; n is a whole number from 2 to 30 with the proviso that if A and B are identical, then n is a whole number from 1 to 15; and wherein the polymer may be capped on one or both ends with a quaternary ammonium group

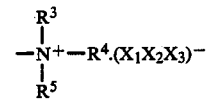

wherein $X_1$, $X_2$ and $X_3$ are as defined above and wherein $R^3$, $R^4$, and $R^5$, which can all be same or different, are alkyl groups having from 1 to 20 carbon atoms and having either 0 or 1 hydroxyl substituent, or $R^3$ and $R^4$ taken together with the nitrogen to which they are attached may form a saturated heterocyclic ring having from 5 to 7 ring atoms.

Substituent A may be substituted or unsubstituted. Preferably, A is substituted by at least one substituent selected from the group consisting of a hydroxyl group and a substituent substituted by at least one hydroxyl group.

Preferred substituents for both the A and B moieties, which can be identical or different, include $C_nH_{2n}OH$, wherein n ranges from 1 to 10, and more preferably $CH_2OH$, and also hydroxyaryl, and more preferably hydroxyphenyl.

DETAILED DESCRIPTION OF THE INVENTION

Ionene polymers belong to a well-known class of compounds, which together with methods for their preparation are described in U.S. Pat. Nos. 3,874,870, 3,931,319, 4,025,627, 4,027,020, and 4,506,081. The trihalides of ionenes, such as the triiodides in particular, can be prepared by replacing the halogen, preferably chloride or bromide, with trihalide anion, as described in U.S. Pat. No. 3,778,476.

For example, a triiodide solution is prepared by mixing iodine and an alkali metal iodide, preferably potassium or sodium iodide, in water. On adding a solution of polymeric quaternary ammonium chloride or bromide to this triiodide solution, a dark solid precipitates. After decanting the aqueous layer, the triiodide compound is obtained. The triiodide compound can be used in the solid form or solubilized in acetone or some other suitable polar organic solvent or combination of solvents to yield an effective formulation.

Formulations of ionene trihalide and in particular, ionene triiodide, can be added to various water systems to control the growth of undesirable microorganisms, including fungi. The effectiveness against fungi that can be obtained is surprising in view of the lack of efficacy of conventional ionenes, i.e., those having single halogen ions as the counter ions to the positive charges, against fungi.

Ionene trihalides, such as the triiodides, can also be used to disinfect or sanitize surfaces. The time required to completely kill bacteria on a hard surface can be much less for the trihalide salt than that for conventional halide salts.

The solid form of the triiodide can be added to water systems, such as cooling towers or swimming pools, to provide a continuous release microorganism control agent.

The ionene trihalides of this invention that are novel differ from those described in the prior art, such as U.S. Pat. Nos. 3,778,476 and 3,898,336, because the B substituent described above contains at least one pendant hydroxyl group, i.e., at least one hydroxyl group substituent attached directly to the main polymer chain (the divalent hydrocarbon radical) or at least one substituent (pendant group) itself substituted by at least one hydroxyl group, the substitutent being attached directly to the divalent hydrocarbon radical. This difference improves the solubility in water and provides an advantage when used in aquatic systems.

Preferred trihalides are poly[(dimethyliminio)-2-hydroxypropylene triiodide] of the formula

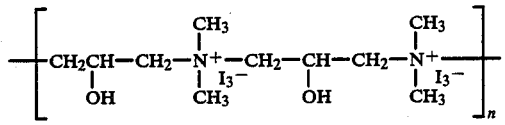

wherein A and B are identical and n is from 1 to 15; poly[oxyethylene(dimethyliminio)hydroxypropylene(-dimethyliminio)ethylene di(triiodide)] of the formula

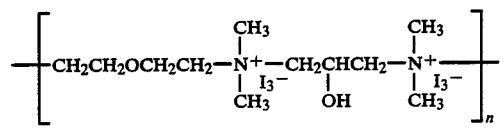

wherein n is from 2 to 30; and poly[2-hydroxyethylene(-dimethyliminio)ethylene(dimethyliminio)-methylene di(triiodide)] of the formula

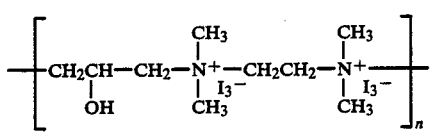

wherein n is from 2 to 30.

The invention will be further clarified by the following examples, which are intended to be merely illustrative of the present invention.

EXAMPLE 1

Preparation of poly[oxyethylene(dimethyliminio)ethylene(dimethyliminio)-ethylene di(triiodide)] (Compound 1)

A solution of 12.7 g (0.05 mole) of iodine and 20.0 g (0.12 mole) of potassium iodide in 1 liter of water was prepared. To the above vigorously-stirred solution were added dropwise 21.6 g (0.05 molar equivalents of chloride ion) of poly[oxyethylene(dimethyliminio)ethylene-(dimethyliminio)ethylene dichloride] (60% aqueous solution available commercially as Busan® 77 polymer). During this addition, a dark brown solid precipitated out of the solution, and the amount of solid increased with the increasing amount of polymer dichloride that was added. After the addition was complete, the reaction mixture was stirred at room temperature for an additional two hours. Most of the aqueous layer was decanted and the precipitate was filtered and collected. A 73.7% yield (35.0 g) of this dark brown solid was obtained. An elemental analysis (in duplicate) of the solid showed it to be poly[oxyethylene(dimethyliminio)ethylene(dimethyliminio)ethylene di(triiodide)]. The results are given in Table 1.

TABLE 1

| Element | % Calculated | % Found (1) | % Found (2) |
|---|---|---|---|
| C | 12.63 | 13.14 | 13.20 |
| H | 2.53 | 2.64 | 2.55 |
| I | 80.21 | 79.23 | 79.14 |
| N | 2.95 | 3.08 | 3.04 |

The solubility of this compound was determined by stirring 1 gram in 1 liter of deionized water for 2 hours. Supernatant solution was analyzed for quaternary ammonium salts using the bromophenol blue titration method and for iodide using a selective ion electrode. The amount of the dissolved polymeric quaternary ammonium triiodide was found to be 183 ppm, which is well above the effective level in water as subsequent examples show. This compound can be formulated at 5% in N-methylpyrollidone using Atlox 3409 surfactant.

EXAMPLE 2

Preparation of poly[(dimethyliminio)-2-hydroxypropylene triiodide] (Compound 2).

The procedure described in Example 1 was followed using poly[(dimethyliminio)-2-hydroxypropylene chloride], a product commercially available as Busan ®1055 polymer.

Elemental analysis of the product gave the expected results, shown in Table 2.

TABLE 2

| Element | % Calculated | % Found |
|---|---|---|
| C | 12.42 | 13.00 |
| H | 2.48 | 2.67 |
| I | 78.88 | 77.58 |
| N | 2.89 | 3.04 |

EXAMPLE 3

Effectiveness of Compound 1 and Compound 2 against bacteria

The effectiveness of the Compounds 1 and 2 prepared in Examples 1 and 2 was determined against *Enterobacter aerogenes* at pH 8.0 using the method described in U.S. Pat. No. 2,881,070 with the modification described in Example 22 of U.S. Pat. No. 4,054,542. Effectiveness of each polymer was determined at various contact times. The results are given in Table 3.

In comparison to these results, the dichloride used as the starting material in Example 1, Busan ® 77 polymer, has an MIC of 10 ppm for 8 hours contact time and 20 ppm for 4 hours contact time.

TABLE 3

Minimum Inhibitory Concentration (MIC) of two triiodinated polymers to produce 90% kill of *Enterobacter aerogenes* in a basal salts solution at pH 8.0 after multiple contact times

| Contact Time | MIC in parts per million | |
|---|---|---|
| (hours) | Compound 1 | Compound 2 |
| 2 | 0.3 | 2 |
| 4 | 0.3 | 2 |
| 6 | 0.3 | 2 |
| 8 | 0.3 | 2 |
| 24 | 0.3 | 2 |

EXAMPLE 4

Disinfectant effectiveness of Compound 1 and Compound 2.

In this example, the effectiveness of the compounds prepared in Examples 1 and 2 was determined against *Staphylococcus aureus* and *Salmonella choleraesuis* using the A.O.A.C. Use-Dilution test described in the Official Methods of Analysis (1984) 14th Ed., AOAC, Washington, DC, Secs. 4.007–4.011. The results are given in Table 4.

TABLE 4

| | Maximum dilution providing kill in 10 of 10 replicates in 10 min. vs. | |
|---|---|---|
| Test material | *Staphylococcus aureus* | *Salmonella choleraesuis* |
| Compound 1 | 1:1000 | 1:1000 |
| Compound 2 | 1:2500 | 1:2500 |

EXAMPLE 5

Zone Inhibition Study with Compounds 1 and 2

The inhibitory properties of the two ionene triiodides prepared in Examples 1 and 2 were assayed against *Enterobacter aerogenes* and *Staphylococcus aureus* using a zone of inhibition technique. In this assay, nutrient agar was inoculated with *E. aerogenes* and poured into a sterile petri dish. When the agar was solidified, a measured disc of the solid test compound was placed on the surface of the inoculated agar. Following incubation, the clear zone surrounding the measured disc was measured. This procedure was repeated with *S. aureus*. Inoculated agar plates to which no test compound was added were included as controls. The results are shown in Table 5.

TABLE 5

Zone of Inhibition of *Enterobacter aerogenes* and *Staphylococcus aureus* by Compounds 1 and 2 after 24 hours incubation.

| | Zone of inhibition in millimeters vs. | |
|---|---|---|
| Test material | *E. aerogenes* | *S. aureus* |
| Control | 0 | 0 |
| Compound 1 | 7 | 5 |
| Compound 2 | Complete | Complete |

EXAMPLE 6

Effectiveness of Compounds 1 and 2 against fungi.

The effectiveness of the compounds prepared in Examples 1 and 2 against the fungus *Aspergillus niger* was determined in a mineral salts medium. The medium is composed of the following:

| | |
|---|---|
| Glucose | 10.0 g |
| Ammonium nitrate | 3.0 g |
| Potassium phosphate ($K_2PO_4$) | 1.0 g |
| Potassium chloride | 0.25 g |
| Magnesium sulfate | 0.25 g |
| Tween 80 | 0.5 g |
| HCl-Trizma buffer | 6.0 g |
| Deionized water | 1000 ml |

Forty-gram portions of the medium are added to 250-ml Erlenmeyer flasks fitted with loose metal caps and then sterilized. The following substances are then added to each bottle in the order listed:

1. Sterile mineral salts solution as required in each individual case to bring the total weight of the contents of each flask to 50 g, after allowing for all subsequent additions specified hereinafter, including inoculation with the aqueous suspension of spores.

2. Solution of toxicant to be evaluated in such individual volumes to give the concentration desired in the test; the amount is computed in parts per million by weight. Duplicate controls containing no toxicant are used.

3. Inoculum consisting of 1 ml of an aqueous suspension of spores and/or mycelial fragments of the test organism.

After the inoculant suspensions of the test fungus have been added, the flasks are incubated at 30±1° C. for a period adequate for growth in the controls. The customary period of observation is 14 days. Growth is recorded at 7 days and 14 days on the basis of the following key:

4 = excellent growth
3 = good
2 = poor
1 = very poor, scant, questionable
0 = no growth A toxicant is considered an effective fungicide if it scores 0 (no growth) at the recommended use concentration at the 14-day observation period. The results of the test with Compound 1 and Compound 2 are given in Table 6. In comparison, the chloride analog of Compound 1, Busan ® 77 polymer, will not control *A. niger* at 1000 ppm, the highest level tested.

TABLE 6
Inhibition of Aspergillus niger by two triiodinated polymers after 14 days.

| Test material | Concentration in ppm | Growth Rating |
|---|---|---|
| Compound 1 | 1 | 4 |
|  | 5 | 4 |
|  | 25 | 0 |
| Compound 2 | 1 | 4 |
|  | 5 | 4 |
|  | 25 | 0 |

EXAMPLE 7

Effectiveness of Compounds 1 and 2 against algae.

The growth inhibiting activity of the compounds made in Examples 1 and 2 was evaluated in Difco Algae Broth, the content of which was as follows:

| Compound | Grams per liter |
|---|---|
| Sodium nitrate | 1.000 |
| Ammonium chloride | 0.050 |
| Calcium chloride | 0.058 |
| Magnesium sulfate | 0.513 |
| Dipotassium phosphate | 0.250 |
| Ferric chloride | 0.003 |

Forty-gram portions of the algae medium were added to 250 ml Pyrex Erlenmeyer flasks fitted with loose metal caps and then sterilized. Each of the following substances was then added to the flasks in the order listed:

1. Sterile algae medium as required to bring the total weight of the contents of each flask to 50 grams, after allowing for all subsequent additions specified hereinafter.
2. Solution of toxicant or control agent to be evaluated in each test, to give the concentration desired in parts per million by weight.
3. *Chlorella pyrenoidosa* and *Phormidium inundatum* in amounts sufficient to give excellent growth in the controls after 14 days. This was achieved by adding 1 milliliter of a 14 day old culture having luxuriant growth. The *Chlorella pyrenoidosa* culture was obtained from American Type Culture Collection No. 7516; *Phormidium inundatum*, Wisconsin No. 1093, was obtained from the University of Washington.

After the inoculum of the test algae was added, the flasks were incubated at a temperature of 28±2° C. under fluorescent illumination of 250 foot-candle intensity (8 hours light, 16 hours darkness) for a period adequate for growth in the controls (those portions of medium which contained no toxicant). Observations of growth were made at 7 day intervals on the basis of the following key:

4=excellent growth
3=good
2=poor
1=very poor, scant, questionable
0=no growth

The results are given in Table 7.

TABLE 7
Inhibition of algae by Compounds 1 and 2.

| Organism | Concentration in ppm | Compound 1 | Compound 2 |
|---|---|---|---|
| Chlorella pyrenoidosa | 1 | 1 | 3 |
|  | 5 | 0 | 0 |
|  | 10 | 0 | 0 |
|  | 25 | 0 | 0 |
| Phormidium inundatum | 1 | 1 | 1 |
|  | 5 | 0 | 0 |
|  | 10 | 0 | 0 |
|  | 25 | 0 | 0 |

What is claimed is:

1. A polymeric quaternary ammonium compound of the formula:

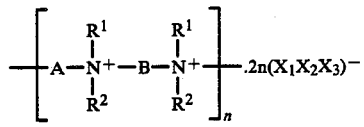

wherein $X_1$, $X_2$ and $X_3$ are each a halogen and can all be the same halogen or different halogens;

$R^1$ and $R^2$, which can all be the same or different, are selected from the group consisting of alkyl groups having from 1 to 20 carbon atoms and having either 0 or 1 hydroxyl substituent, a benzyl group, and a benzyl group bearing on the benzene moiety one alkyl group having from 2 to 20 carbon atoms;

A is selected from the group consisting of a divalent hydrocarbon radical containing 1 to 10 carbon atoms and a divalent hydrocarbon radical containing 1 to 10 carbon atoms and also containing an oxygen atom as an either group; wherein A may be identical with or different from B, wherein B is defined as follows;

B is a divalent hydrocarbon radical containing 1 to 10 carbon atoms, said divalent hydrocarbon radical being substituted by at least one substituent selected from the group consisting of a hydroxyl group and a substituent substituted by at least one hydroxyl group; and n is a whole number from 2 to 30, with the proviso that, when A and B are identical, n is a whole number from 1 to 15;

and wherein said polymer may be capped on one or both ends with a quaternary ammonium group of the formula:

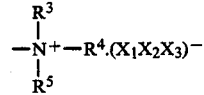

wherein $X_1$, $X_2$ and $X_3$ are as defined above; and $R^3$, $R^4$ and $R^5$, which can all be the same or different, are alkyl groups having from 1 to 20 carbon atoms and having either 0 or 1 hydroxyl substituent, or $R^3$ and $R^4$ taken together with the nitrogen atom to which they are attached may form a saturated heterocyclic ring having from 5 to 7 ring atoms.

2. The polymeric quaternary ammonium compound of claim 1, wherein said divalent hydrocarbon radical A is substituted by at least one substituent selected from the group consisting of a hydroxyl group and a substituent substituted by at least one hydroxyl group.

3. The polymeric quaternary ammonium compound of claim 1, wherein $X_1$, $X_2$ and $X_3$ are all iodide.

4. The polymeric quaternary ammonium compound of claim 3, wherein A is an alkylene radical and wherein B is a hydrocarbon radical selected from the group consisting of alkylene, aryl, arylalkylene and alkylenearylalkylene, said hydrocarbon radical B being substituted by at least one substituent selected from the group consisting of a hydroxyl group attached directly to said hydrocarbon radical and a substituent substituted by at least one hydroxyl group, said substituent being attached directly to said hydrocarbon radical.

5. The quaternary ammonium compound of claim 4, wherein at least one of A and B is substituted by at least one substituent selected from the group consisting of —$C_nH_{2n}OH$ wherein n ranges from 1 to 10, and hydroxyaryl.

6. The quaternary ammonium compound of claim 5, wherein at least one of A and B is substituted by at least one substituent selected from the group consisting of —$CH_2OH$ and hydroxyphenyl.

7. Poly(dimethyliminio)-2-hydroxypropylene triiodide.

8. Poly[oxyethylene(dimethyliminio)hydroxypropylene (dimethyliminio)ethylene di(triiodide)].

9. Poly[2-hydroxyethylene(dimethyliminio)ethylene(dimethyliminio)ethylene(dimethyliminio)methylene di(triiodide)].

* * * * *

UNITED STATES PATENT AND TRADEMARK OFFICE
CERTIFICATE OF CORRECTION

PATENT NO. : 4,960,590

DATED : October 2, 1990

INVENTOR(S) : C. George Hollis, et al.

It is certified that error appears in the above-identified patent and that said Letters Patent is hereby corrected as shown below:

Claim 7, column 10, line 8,
"Poly(dimethyliminio)..." should be
--Poly[(dimethyliminio)...--;
and on line 9, "dide" should be followed by
--]--.

Claim 8, column 10, lines 10-11,
"hydroxypropy-lene" should be
--hydroxypropyl-ene--.

Claim 9, column 10, lines 12-14, "Poly[2-hydroxyethylene(dimethyliminio)e-thylene(dimethyliminio)ethylene(dimethyliminio)-methylene di(triiodide)]." should be
--Poly[2-hydroxyethylene(dimethyliminio)-ethylene-(dimethylininio)methylene di(triiodide)].--

Signed and Sealed this

Twenty-first Day of January, 1992

Attest:

HARRY F. MANBECK, JR.

*Attesting Officer*      *Commissioner of Patents and Trademarks*